United States Patent [19]

Moroz

[11] 4,046,635

[45] Sept. 6, 1977

[54] METHOD FOR DETECTING ENZYMES CAPABLE OF DIGESTING FIBRINOGEN OR FIBRIN

[75] Inventor: Leonard Arthur Moroz, Westmount, Canada

[73] Assignee: Canadian Patents and Development Limited, Ottawa, Canada

[21] Appl. No.: 608,237

[22] Filed: Aug. 27, 1975

[51] Int. Cl.$^2$ .............................................. G01N 31/14
[52] U.S. Cl. .......................... 195/103.7; 195/103.5 R; 195/127
[58] Field of Search ............... 195/103.5 R, 127, 103.7

[56] References Cited

U.S. PATENT DOCUMENTS

| 3,639,558 | 2/1972 | Csizmas et al. | 195/103.5 R |
| 3,778,352 | 12/1973 | Bishop et al. | 195/103.5 R |

OTHER PUBLICATIONS

Genton et al., "Assay of Plasma Thrombolytic Activity with Fluorescein-Labelled Clots," J. Lab. & Clin. Med., 1964, pp. 313-320.
Alkjaersig et al., "The Mechanism of Clot Dissolution by Plasmin," J. Of Clinical Investigation 38, (1959), pp. 1086-1095.
Unkeless et al., "An Enzymatic Function Associated with Transformation of Fibroblasts by Oncogenic Viruses," J. of Experimental Medicine 137, (1973), pp. 85-111.

*Primary Examiner*—Alvin E. Tanenholtz
*Assistant Examiner*—C. A. Fan
*Attorney, Agent, or Firm*—Cushman, Darby & Cushman

[57] ABSTRACT

A method for detecting and measuring the activity of enzymes capable of digesting fibrinogen or fibrin and for detecting and measuring the activity of enzyme activators and enzyme inhibitors of said enzymes, by incubating an unknown enzyme sample in a humid labelled fibrinogen or labelled fibrin coated test apparatus, isolating the labelled degradation products of fibrinogen or fibrin released by the unknown enzyme sample and measuring the labelled degradation products of fibrinogen released by the unknown sample.

10 Claims, No Drawings

METHOD FOR DETECTING ENZYMES CAPABLE OF DIGESTING FIBRINOGEN OR FIBRIN

The present invention relates to a method for measuring and detecting enzymes capable of digesting fibrinogen or fibrin and for measuring and detecting activators and inhibitors of said enzymes.

PRIOR ART

Conversion of fibrinogen in plasma to fibrin (clot formation) is an important physiological intravascular hemeostatic mechanism. Plasminogen is the proenzyme in plasma which, upon conversion to its active form, plasmin, is considered responsible for the proteolytic digestion of fibrin clots resulting from either physiological or pathological activation of the coagulation process in blood vessels (conversion of soluble fibrinogen to insoluble fibrin). Because of the importance of this proteolytic process in relation to cardiovascular disease (arteriosclerosis, thromboembolic disease) and to certain bleeding disorders, there is an important place for methods which rapidly, conveniently, and accurately assess fibrinolytic activity in blood, and which permit the identification of new drugs which inhibit or activate either the enzymatic activity of plasmin, or the conversion of the plasma proenzyme (plasminogen) to the active enzyme. Such assessments are optimally based on the degradation of the physiological substrate, fibrin, by either purified plasmin, or plasma samples which contain this enzyme.

One method for assessing the degradation of fibrin by plasmin is based on the formation of a plasma clot (or a clot formed from the euglobulin fraction of plasma), either spontaneously, or by the action of the enzyme, thrombin, with measurement of the time required for spontaneous lysis of the clot. Variations of this methodology such as dilute blood clot lysis time and euglobulin clot lysis time have been employed clinically for years. This method has the disadvantage of being relatively insensitive to low levels of plasmin and is time-consuming.

Another method is based on the lysis of fibrin, incorporated into a plate format, by plasma or other biological fluids, or purified enzymes, introduced into wells cut in the plate (fibrin plate method). Such a method, based on measurement of the diameter of the zone of lysis centrifugally from the sample wells, is widely applied clinically in the form of commercial plates (Enzo-diffusion fibrin plate test) marketed by the Travenol Division of Hyland Laboratories, Costa Mesa, California. This method is described *Arch. Biochem Biophys* 40:346,1952. The disadvantage of this method is that results take at least six hours in general, and lacks sensitivity.

Another method comprises the labelling of fibrinogen with radioiodine or a fluorochrome, conversion of the labelled fibrinogen to a fibrin clot, immersion of this clot as substrate in the plasma or other body fluid to be tested, and quantitation of the labelled degradation products released from the clot by fibrinolytic enzymes. Although employed in research studies, such methods have not been widely employed clinically. This method is time consuming and is not readily amenable to the rapid screening of hundreds of samples. This method is described in *Journal of Clinical Investigation*, 38:1086–1095, 1959, ALKJAERSIG et al.

In *J. Lab & Clin Med*, 1964, 313–320, Genton et al, there is disclosed that casein, a non-physiological protein substrate which is digested by plasmin, has been labelled with radioiodine, and covalently coupled to agarose beads. Release of labelled degradation products during incubation with plasma or fibrinolytic enzymes is measured. This method has had only limited research application. This method employs a nonphysiological substrate for assessment of fibrinolysis, and has not been applied clinically or commercially to any significant extent.

Plastic culture dishes coated with 125 I labelled fibrin have been used to assay fibrinogenetic enzymes produced by cells in tissue culture (*Journal of Experimental Medicine*, 137:85–111, 1973, Unkeless et al). However, it would appear that degradation products obtained may be contaminated with non-degraded substrate, decreasing the usefulness of the method.

Finally, since plasmin is an esterase, a variety of methods for its assay have been developed, all based on the hydrolysis of simple esters or synthetic substrates. These have had limited research application in the screening of inhibitors and activators of plasmin-mediated proteolysis.

THE INVENTION

In accordance with the present invention there is now provided an improved method for detecting or measuring enzymes capable of digesting fibrinogen or fibrin and for detecting or measuring activators and inhibitors of said enzymes. The improved method of the present invention affords, amongst other advantages, easy separation of residual substrate and degradation products, quantitative evaluation of the degradation products, simplicity, speed, sensitivity and versatility.

Broadly, in accordance with the present invention, a labelled fibrinogen or fibrin attached to a solid phase provides a suitable substrate for enzymes capable of digesting fibrinogen or fibrin thus providing ready separation and quantitation of degradation products released from these proteins by the action of the enzymes. Thus the method of the present invention provides an efficient way to evaluate enzymes found in any biological system particularly with regard to the ability of said enzymes to attack fibrin which is the main constituent of blood clots.

More specifically, the invention comprises incubating a humid labelled fibrinogen or fibrin coated test apparatus with an unknown enzyme sample thereby to cause the unknown enzyme to digest labelled fibrinogen of fibrin, separating the released labelled degradation products of fibrinogen or fibrin, said degradation products being substantially free of initial fibrinogen or fibrin, and measuring the labelled degradation products of fibrinogen or fibrin released by the unknown sample.

When it is desired to carry out the testing procedure of the present invention on labelled fibrin, a labelled fibrinogen coated test apparatus is treated with a solution of thrombin thereby converting the labelled fibrinogen to labelled fibrin. As can be appreciated the improved procedure of the present invention affords a choice of two labelled test materials for the evaluation of any unknown enzyme.

Furthermore the present invention provides a most suitable test which will find application in that part of the clinical industry directed at the isolation and purification of plasminogen activators for use in the treatment of thromboembolic and other cardiovascular diseases, and in finding and developing new drugs which enhance fibrinolysis, for treatment of conditions in which fibrinolysis is pathologically increased. A pertinent example is the activity in developing urokinase, a clinically promising plasminogen activator. The method of the present invention is the most convenient, sensitive and rapid assay method available for screening both types of pharmaceuticals.

Furthermore the availability of the test apparatus as assay tubes in kit form will satisfy the needs of research workers dealing with basic aspects of the inhibition and activation of fibrinolysis.

Also in clinical application the method of the present invention has demonstrated the feasibility of using the improved test for assessment of fibrinolytic activity in plasma samples, and for the quantitation of plasmin inhibitors in plasma. The only widely applied method (fibrin plate method) is less sensitive, more cumbersome, and more time consuming.

The test apparatus used to carry out the present invention may be any of the test apparatus used in radioimmunoassay. For example the test apparatus may be a polymeric test tube, a bead or an insert having an affinity for fibrinogen or fibrin. As an example of the polymeric material used to manufacture the test tube there may be mentioned polystyrene, polyethylene, polypropylene, nitrocellulose, copolymers of acrylonitrile with styrene such as polystyrene-co-acrylonitrile, with the polystyrene being the preferred polymeric material.

As starting material the fibrinogen is prepared from the plasma of human or other species by methods known in the art. Nevertheless, precaution should be exercised to insure that the fibrinogen is free of contaminating enzymes capable of digesting fibrinogen. This is done by fractionating procedures known in the art.

The starting fibrinogen is labelled by any of different procedures. For example radioactive labelled fibrinogen can be obtained by reacting the fibrinogen with a suitable isotope such as $I^{125}$, $I^{131}$, $C^{14}$ or $H^3$. A particularly suitable isotope is a radioactive isotope of iodine such as $I^{125}$, since labelling with this isotope is simple and as many hospitals laboratories now have the equipment necessary to measure this isotope. It should also be appreciated labelled fibrinogen can also be obtained by deriving fibrinogen from animals which have been submitted to a prior injection of a radioactive precursor.

Also included in the expression "labelled fibrinogen" is any fibrinogen in which a chromogenic chemical product has been incorporated by known methods. As an example of suitable chromogenic chemical product there may be mentioned fluorescein isothiocyanate and fluorescamine.

When it is desired to test the unknown enzyme with labelled fibrin, the labelled fibrinogen coated test apparatus is reacted with thrombin thus converting the labelled fibrinogen to labelled fibrin. According, whenever used the expression labelled fibrinogen or labelled fibrin is used herein it is intended to include fibrinogen or fibrin labelled with a radioactive isotope or with a chromogenic chemical product.

In the first step, the polymeric test apparatus, for example, a test tube is coated with the labelled fibrinogen. The amount of labelled fibrinogen will be dependent on the polymeric material, its shape and surface. As an example, there could be used 0.1 ml of a labelled fibrinogen solution containing 100 μg labelled fibrinogen/ml for a tube having a diameter of 12 mm and having a round bottom and made of polystyrene. As a general guideline the pH of the labelled fibrinogen solution should be such as to avoid denaturation of the fibrinogen. As an example it has been found that labelled fibrinogen buffered with 0.015M phosphate buffer solution of pH 8 is suitable. The coating time can extend up to 24 hours, though maximum coating is obtained after about 4 hours at room temperature. Even coating of the coated surface can easily be obtained by rotating the tube while coating at an angle of about 45° with a revolution of about 5 r.p.m.

The thus labelled fibrinogen coated test tube is then treated with an extraneous protein to cover any polymeric surface sites not coated by labelled fibrinogen. This coating is carried out by inserting a greater volume of extraneous protein solution than the volume of labelled fibrinogen and after standing for a short period of time the thus coated tube is washed. The purpose of this protein coating is to insure that when the unknown enzyme sample is added to the tube there will not be any binding of said enzyme to any part of the polymeric surface of the tube not coated with labelled fibrinogen. As extraneous protein, there may be mentioned bovine serum albumin and such other proteins not significantly digested by enzymes which digest fibrinogen or fibrin. As an example, an albumin solution containing 10 mg/ml of albumin dissolved in 0.015M phosphate buffer at pH 8 has been found suitable.

After coating the labelled fibrinogen coated test tube with the extraneous protein, any surplus of the protein is removed by washing by any well known method. For example, washing can be effected with a buffer solution of 0.015 molar Tris i.e. 2-amino-2-hydroxymethyl-1,3-propanediol and 0.15 molar NaCl adjusted to pH 7.4 with HCl.

The thus labelled fibrinogen coated test tube is ready for use in accordance with the novel process of the present invention. Nevertheless if the test is to be carried out with labelled fibrin, then the labelled fibrinogen coated test apparatus is treated with a thrombin solution to effect the conversion of labelled fibrinogen to labelled fibrin. Excess thrombin is then removed by washing and the labelled fibrin coated test apparatus is then ready for use.

It should be noted that if the labelled fibrinogen or fibrin coated test apparatus is not to be used immediately after coating, the coating should be kept in humid (moist) conditions such as by storing in contact with a buffered solution which may contain a preservative.

A sample of the unknown enzyme, enzyme activator or enzyme inhibitor is then introduced in the labelled fibrinogen or labelled fibrin coated test apparatus and incubated for a suitable time whereby the unknown enzyme will digest the labelled fibrinogen or labelled fibrin thereby releasing into solution labelled degradation products which can then be separated and measured qualitatively and quantitatively.

The term "unknown enzyme" when used herein is intended to be construed in its broadest sense, i.e. it is to include any enzyme capable of digesting fibrinogen or fibrin. This term therefore includes a pure enzyme as fractionated from any source such as blood, body fluids or tissues, a mixture of known and unknown enzymes, a partially purified enzyme preparation or a fraction possessing enzymatic activity which has been derived from whole blood, any of its components, any body fluids or body tissues.

The volume of the unknown enzyme sample is such that it is contained within that portion of the test apparatus which has been coated with labelled fibrinogen. After introduction of the unknown sample the test apparatus is incubated at a suitable temperature, for example, 37° C for a suitable time.

During incubation the enzyme will digest the labelled fibrinogen or labelled fibrin thereby releasing labelled degradation products of fibrinogen or fibrin. As is known each enzyme exerts a characteristic degradation effect on fibrinogen or fibrin and this feature can now be utilized as a means for detecting and measuring such activity by counting the radiation, or by chromographic analysis followed by subsequent analysis of the degradation products.

Also in accordance with the present invention there is provided a test kit for detecting and measuring the activity of enzymes capable of digesting fibrinogen or fibrin and for detecting the activity of enzyme activators and enzyme inhibitors. The kit comprises a polymeric test apparatus coated with labelled fibrinogen and coated with an extraneous protein at sites not coated with labelled fibrinogen. The kit may also include a thrombin solution for converting the labelled fibrinogen to labelled fibrin when it is desired to carry out the test with labelled fibrin.

EXAMPLE 1

Detection and measurement of the enzymatic activity of plasmin

Preparation of $^{125}$I-labelled fibrinogen

Fibrinogen, was prepared from normal human plasma by known procedures, contaminating plasminogen and plasmin removed by passage through a column of lysyl-Sepharose prepared by the well known cyanogen bromide method as described by Deutsch and Mertz. Fibrinogen was radioactively labelled with iodine-125 by the chloramine T method of Hunter and Greenwood.

Preparation of $^{125}$I-labelled fibrinogen and fibrin coated tubes $^{125}$I-labelled fibrinogen prepared in the manner described was adjusted to a specific activity of 50,000 to 75,000 counts/min/μg fibrinogen by addition of unlabelled fibrinogen, and diluted to a concentration of 100 μg fibrinogen/ml and made 0.015 molar in phosphate at pH 8. Aliquots of this solution (0.1 ml) were introduced into polystyrene test tubes (12 × 75 mm, round bottom), each tube receiving 10 μg of $^{125}$I-labelled fibrinogen. The tubes and contents are rotated in a tissue culture rotator at room temperature, and an angle of 45°, at 5 r.p.m.; for 3 hours, following which tube contents were aspirated by suction, and replaced by 0.5 ml of a bovine serum albumin solution (10 mg/ml) in buffer, and allowed to stand for 20 minutes at room temperature. Following this, tube contents were removed by aspiration, and the $^{125}$I-labelled fibrinogen coated tubes washed with buffer. For conversion of the $^{125}$I-labelled fibrinogen to fibrin, a thrombin solution 0.2 ml (10 units/ml) was introduced into each test apparatus, and incubated at 37° for 30 minutes, following which the $^{125}$I-labelled fibrin coated tubes were washed 5 to 6 times with buffer or tap water, and stored, after filling with buffer containing 0.1% sodium azide by weight, at 4° until required for use. Tubes prepared in this way were coated with approximately 1.5 μg of $^{125}$I-labelled fibrin (30,000 to 120,000 counts/min/μg).

$^{125}$I-labelled fibrin coated tubes prepared in this manner were used to detect and measure plasmin, an enzyme present in human plasma, and capable of digesting fibrin. Aliquots (0.2 ml) of buffer solution containing increasing concentrations of purified plasmin prepared by known procedures) were introduced into the test apparatus and incubated at 37° for 30 minutes, following which the tube contents were diluted by addition of 2.0 ml of buffer solution and quantitatively transferred to an untreated test tube and the radioactivity of the tube contents, representing the degradation products released from the $^{125}$I-labelled fibrin bound to the test apparatus, was quantitated by a conventional method (gamma scintillation spectrometer). As indicated in Table I, increasing concentrations of plasmin added to the test apparatus results in increasing release of radioactivity representing degradation products released from the fibrin substrate. Digestion of fibrin is virtually linear over the concentration range shown, and the method is capable of detecting at least 0.2 μg plasmin/ml.

TABLE I

| Detection and Measurement of Plasmin | |
|---|---|
| Plasmin (μg) | $^{125}$I-fibrin digested (counts/min) |
| 0.2 | 2,258 |
| 0.4 | 4,703 |
| 0.6 | 7,509 |
| 1.0 | 13,152 |

EXAMPLE 2

Detection and measurement of enzymes capable of activating plasminogen to plasmin (plasminogen activators)

Proceeding in the same manner as described above, mixtures of the plasmin precursor, plasminogen (prepared by known procedures), and the plasminogen activator, urokinase were introduced into the test apparatus in place of plasmin.

Although the precursor of plasmin, plasminogen, does not digest fibrin, it may be converted to active plasmin by activators such as the enzyme urokinase. The generation of plasmin from plasminogen, as detected by the activity of plasmin generated, consequently provides an indirect method of detecting and measuring urokinase or other activators. Plasminogen (6 μg) was incubated with urokinase (at the final concentrations shown in Table II), in a final volume of 0.2 ml, for 30 minutes at 37° C.

TABLE II

| Detection and Measurement of an Activator of Plasminogen | |
|---|---|
| Urokinase (CTA units/ml) | $^{125}$I-fibrin digested (counts/min) |
| 0.004 | 0 |
| 0.040 | 1,054 |
| 0.400 | 2,673 |
| 4.000 | 12,664 |
| 40,000 | 14,106 |

As shown in Table II the test apparatus provides a sensitive method for detecting the presence of factors which activate plasminogen to plasmin. A urokinase concentration of 0.04 CTA units/ml readily detectable, indicating the high sensitivity of the method for such activity.

EXAMPLE 3

Detection and measurement of chemical substances which inhibit the digestion of fibrin by plasmin Proceeding as in Example 1, except that samples introduced into the test apparatus consisted of purified plasmin and varying amounts of epsilon-amino caproic acid (EACA), a known inhibitor of plasmin action, it is possible to determine whether a chemical substance is capable of inhibiting the action of an enzyme which is capable of digesting fibrin, and the concentration of the substance required to inhibit a given concentration of the enzyme. This is illustrated in Table III.

TABLE III

Detection and Measurement of the Activity of an Inhibitor of the Digestion of Fibrin by Plasmin

| EACA (molar) | $^{125}$I-fibrin digested (counts/min) |
|---|---|
| $10^{-3}$ | 0 |
| $10^{-4}$ | 0 |
| $2 \times 10^{-5}$ | 752 |
| $10^{-5}$ | 2,531 |
| $2 \times 10^{-6}$ | 5,413 |
| $10^{-6}$ | 5,569 |
| $10^{-7}$ | 5,618 |

Plasmin (0.1 μg) and sufficient EACA to yield the final concentrations indicated in Table III, were introduced into the test apparatus in a final volume of 0.2 ml of buffer solution. This indicates the feasibility of rapidly and specifically identifying chemical substances capable of inhibiting the action of plasmin and other enzymes which digest fibrin, which is of obvious importance to pharmaceutical screening programs for such chemical substances.

EXAMPLE 4

Detection and measurement of the capacity of human plasma to digest fibrin

Proceeding as in Example 1, except that in place of purified plasmin, samples (0.2 ml) of normal human plasma are introduced into the test apparatus, and incubated for varying periods of time at 37° C, it is shown in Table IV that significant digestion of $^{125}$I-labelled fibrin by normal human plasma is detectable after a twenty minute incubation. This is not conveniently done by presently available methods, which require incubation times ranging from hours to days for the detection of comparable digestion of fibrin by normal human plasma.

TABLE IV

Detection and Measurement of the Capacity of Human Plasma to Digest Fibrin

| Incubation time (minutes) | $^{125}$I-fibrin digested (ng) |
|---|---|
| 20 | 13.2 |
| 40 | 26.5 |
| 60 | 38.1 |

EXAMPLE 5

Detection and measurement of normal inhibitors of fibrinolytic enzymes present in normal human plasma It is known that normal plasma contains abundant inhibitor which normally regulate the enzymatic activity of plasmin and qualitative or quantitative variations in such inhibitors may be of clinical importance. The method described here is capable of detecting and quantitating such inhibitors by proceeding as in Example 1, except that in place of purified plasmin alone, the samples introduced into the test apparatus consist of purified plasmin and serial dilutions of the plasma to be tested. Into the test apparatus was introduced a known amount of plasmin (0.1 ml of a solution containing 10 μg plasmin/ml), together with 0.1 ml of buffer solution, or 0.1 ml samples of normal human plasma serially diluted with that buffer.

TABLE V

Detection and Measurement of Inhibitors of Fibrin in Normal Plasma

| Digestion by Plasma | $^{125}$I-fibrin digested (ng) |
|---|---|
| Plasmin plus buffer solution | 315 |
| Plasmin plus diluted plasma | |
| Plasma dilution 1:300 | 310 |
| Plasma dilution 1:100 | 211 |
| Plasma dilution 1:30 | 42 |
| Plasma dilution 1:10 | 11 |
| Plasma dilution 1:3 | 5 |

As shown in Table V, inhibition of plasmin digestion of fibrin is apparent at lower plasma dilutions, which inhibition is no longer apparent at higher dilutions. For example, at a dilution of 1:300, digestion in the presence of diluted plasma is virtually identical to that obtained with plasmin alone. It is also possible to use this method to identify and quantitate individual inhibitors of plasmin during their purification from plasma.

I claim:

1. A method for detecting and measuring enzymes capable of digesting fibrin and for detecting and measuring activators and inhibitors of enzymes capable of digesting fibrin which comprises:
   a. coating at room temperature a water-insoluble polymer test apparatus with a buffered solution of a radioactive tracer labelled enzyme-free human fibrinogen to produce a moist coating;
   b. reacting said moist coating with a thrombin solution thereby converting the labelled fibrinogen to labelled fibrin;
   c. contacting said coating of radioactively labelled fibrin with a sample of the unknown enzyme or a mixture of a known enzyme capable of digesting fibrin and the unknown enzyme activator or a mixture of a known enzyme capable of digesting fibrin and the unknown enzyme inhibitor;
   d. incubating said sample in contact with said coating;
   e. washing the test apparatus with a buffered solution and recovering the solution containing the radioactively digested products released by said sample;
   f. counting radiation emitted by said digested and released fibrin and comparing said counts with the number of counts from the coated test apparatus prepared in Step (a).

2. The method of claim 1, wherein said unknown enzyme sample is blood.

3. The method of claim 1, wherein said unknown enzyme sample is a biological fluid.

4. The method of claim 1, wherein said unknown enzyme sample is a solution of at least one enzyme.

5. The method of claim 1, wherein said unknown enzyme sample is a known amount of an enzyme in admixture with an unknown sample containing inhibitors of activators of said known enzyme.

6. A method for detecting and measuring enzymes capable of digesting fibrinogen and for detecting and measuring activators and inhibitors of enzymes capable of digesting fibrinogen which comprises:
   a. coating at room temperature a water-insoluble polymer test apparatus with a buffered solution of a radioactive tracer labelled enzyme-free human fibrinogen to produce a moist coating;

b. contacting said moist coating of radioactively labelled fibrinogen with a sample of the unknown enzyme or a mixture of a known enzyme capable of digesting fibrinogen and the unknown enzyme activator or a mixture of a known enzyme capable of digesting fibrinogen and the unknown enzyme inhibitor;

c. incubating said sample in contact with said coating;

d. washing the test apparatus with a buffered solution and recovering the solution containing the radioactive digested products released by said sample;

e. counting radiation emitted by said digested and released products of fibrinogen and comprising said counts with the number of counts from the coated test apparatus prepared in Step (a).

7. The method of claim 6, wherein the unknown enzyme sample is blood. radioactive 8. The method of claim 6, wherein the unknown enzyme sample is a biological fluid.

9. The method of claim 6, wherein the unknown enzyme sample is a solution of at least one enzyme.

10. The method of claim 6, wherein the unknown enzyme sample is a known amount of an enzyme in admixture with an unknown sample containing inhibitors or activators of said known enzyme.

* * * * *